United States Patent [19]

Murakoshi et al.

[11] 4,304,490
[45] Dec. 8, 1981

[54] SPECTROPHOTOMETER

[75] Inventors: Takeo Murakoshi; Isao Nemoto; Shigeo Tohyama; Nobuo Akitomo, all of Katsuta, Japan

[73] Assignee: Hitachi, Ltd., Tokyo, Japan

[21] Appl. No.: 87,787

[22] Filed: Oct. 24, 1979

[30] Foreign Application Priority Data

Oct. 30, 1978 [JP] Japan ................................. 53/133457
Nov. 8, 1978 [JP] Japan ................................. 53/136726

[51] Int. Cl.$^3$ ........................ G01J 3/42; G01N 21/01
[52] U.S. Cl. .................................... 356/319; 356/244
[58] Field of Search .............................. 356/319–325, 356/244, 96, 39, 40, 51, 367, 368, 408–415; D10/46; 49/404, 413, 449, 451

[56] References Cited

U.S. PATENT DOCUMENTS 3,877,817  4/1975  Ralston ............................... 356/319

OTHER PUBLICATIONS

Catalog No. C-1000, Shimadzu Model QV-50 spectrophotometer, received Group 250 Nov. 18, 1968.

*Primary Examiner*—F. L. Evans
*Attorney, Agent, or Firm*—Craig and Antonelli

[57] ABSTRACT

In a spectrophotometer including a housing, an optical system mounted in the housing and a specimen chamber formed by partitioning a part of the housing for mounting therein a sample cell, the specimen chamber is formed with an opening through which the sample cell is mounted and dismounted and a cover plate is mounted so as to be slidably movable between a closing position where the opening of the chamber is wholly covered by the cover plate and an opening position where the specimen chamber is accessible from outside of the housing.

10 Claims, 13 Drawing Figures

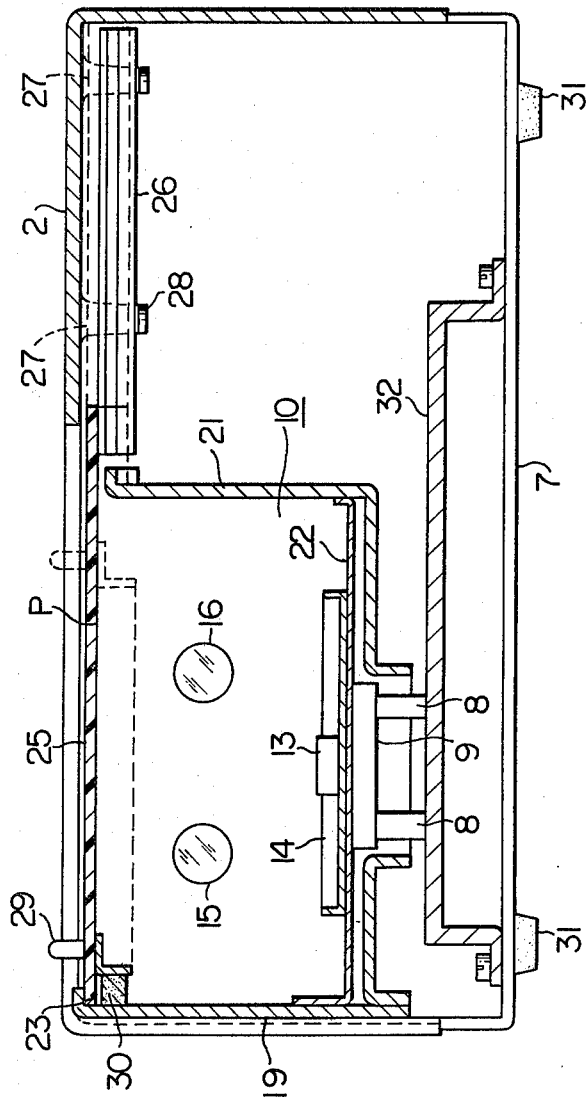
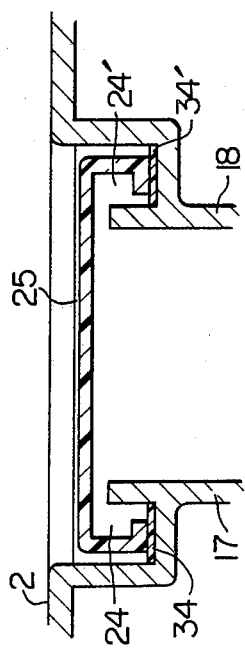
FIG. 5
FIG. 6

SPECTROPHOTOMETER

BACKGROUND OF THE INVENTION

1. Field of the Invention

The invention relates to a spectrophotometer and, more particularly, to a spectrophotometer having an improved specimen chamber.

2. Description of the Prior Art

In a spectrophotometer, especially one using visible and/or ultraviolet light beams, of the type in which a specimen chamber is provided for mounting a specimen cell, an optical system is designed so that an optical path of a measuring light beam crosses the specimen cell mounted in the specimen chamber, and the specimen chamber is provided with an opening through which a sample is mounted or dismounted to and from the specimen chamber, a cover plate is generally provided to cover the opening for shielding the specimen chamber from external light during measurement. This is because in the spectrophotometer using visible and/or ultraviolet light rays, the leakage of external light into the specimen chamber often causes measurement errors greater than tolerable limits. Therefore, it is necessary to seal the specimen chamber substantially completely from external light by covering the opening with the cover plate when the measurement is conducted. If the mounting and dismounting of samples to the specimen chamber are required repeatedly many times, the cover plate is also required to be opened and closed repeatedly many times. Therefore, the cover plate is desired to be supported by the spectrophotometer body even when it is opened, for convenience of its handling. In the conventional spectrophotometers of this type, therefore, the cover plate is pivotably mounted to one of the specimen chamber walls defining the opening, such that it is movable between an opening position where the specimen chamber is open and a closing position where the specimen chamber is closed. However, such spectrophotometers have various disadvantages. First, in order to completely seal the specimen chamber from external light at the pivotal coupling part using hinges, for instance, between the cover plate and the chamber wall, the structure of the coupling part is considerably complicated. Also, it is not easy to remove the cover plate from the chamber wall. Thus, in order to open the opening of the specimen chamber for changing sample cells, the cover plate must be rotated by more than 90° from the closing position to the opening position. After change of the specimens, the cover plate must be returned to the closing position again. When many samples are measured but the time required for measuring each sample is relatively short, the cover plate must be opened and closed frequently in a short time. Therefore, such a large motion required for each opening or closing of the cover plate is troublesome for an operator, and it is disadvantageous that a large space is necessary for allowing such a large motion of the cover plate. In addition, the spectrophotometer is usually provided with a pen-write recorder on one side of the specimen chamber, and the recording paper moves over a part of the specimen chamber. Accordingly, the recording paper is obstructive to the opening and closing of the cover plate. This makes the opening and closing operations more troublesome. A high performance spectrometer generally has various attachments such as a rotating cell holder, a flow cell device, a thermostat cell holder, an integrating sphere which are selectively mounted in the specimen chamber when conducting specific measurements. Some of the attachments are large in size and prevent, when mounted in the chamber, the cover plate from being closed. Therefore, the measurement using such attachments must be done by shielding the chamber from external light with a suitable material other than the cover plate, while it is held at the opening position. However, this is also troublesome, because the cover plate located at the opening position is obstructive of the measures for light-shielding.

SUMMARY OF THE INVENTION

Accordingly, an object of the invention is to provide a spectrophotometer of the type as mentioned above with a specimen chamber having a cover plate which is easily opened or closed without requiring a large space for the opening and closing operations and capable of substantially complete shielding of the specimen chamber from external light.

Another object of the invention is to provide a spectrophotometer of the type as mentioned above with a specimen chamber having a cover plate which is normally mounted to and readily dismounted from the specimen chamber for making it easy to mount various attachments into the specimen chamber without degrading the capability of shielding the specimen chamber from external light.

To achieve the above objects, there is provided a spectrophotometer including a housing, an optical system mounted in the housing for generating a measuring light beam, a specimen chamber provided in the housing for mounting therein a sample cell to be analyzed by applying thereto the measuring light beam, the specimen chamber being formed with an opening through which the chamber is accessible from outside of the housing for mounting or dismounting the sample cell, a generally rectangular cover plate made of an opaque material and adapted to cover the opening of the specimen chamber, and means for mounting the cover plate so as to be slidably movable between a closing position where the cover plate wholly covers the opening thereby shielding the specimen chamber from an external light and an opening position where the specimen chamber is accessible from outside of the housing.

BRIEF DESCRIPTION OF THE DRAWINGS

FIGS. 3 to 5 show cross sectional views taken along lines III—III, IV—IV and V—V in FIG. 1.

FIGS. 6 to 9 show cross sectional views of modifications of the mounting structure of a cover plate of the specimen chamber.

DESCRIPTION OF THE PREFERRED EMBODIMENTS

Figure 1:
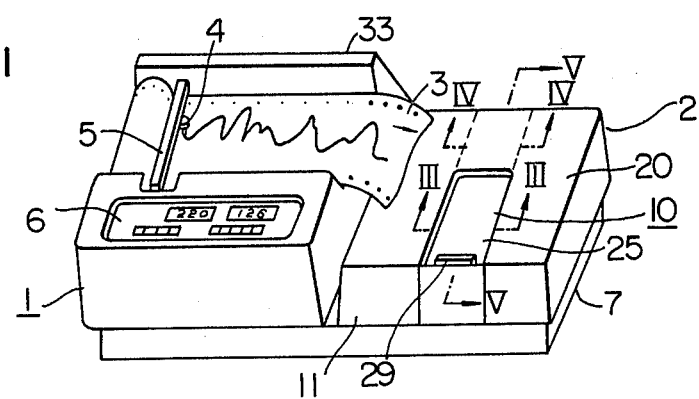
FIG. 1 shows a general view of a spectrophotometer of the present invention.

FIG. 1 shows a perspective view of one embodiment of a spectrophotometer according to the invention. An electric system and an optical system of the spectrophotometer are mounted in a housing including a bottom plate 7 and a cover 2. The bottom plate 7 and the cover 2 are preferably made of fiber reinforced plastic. The housing includes a section 1 enclosing a monochromator body for producing a light beam having a specific wavelength and the electric system associated therewith, a section 11 enclosing a sector to cause the light beam obtained from the monochromator to be divided into two separate light paths, a section 20 enclosing a detector, and a specimen chamber 10 disposed between the sections 11 and 20 for mounting a sample cell to be analyzed and a reference cell. The section 1 includes a recorder 5 with a movable pen 4 for recording measuring results on a recording sheet, a panel 6 with operation switches and an indicator for indicating the wavelength of the measuring light and a measured absorbance. A part of the section 11 is partitioned to mount a light source device 60 of the monochromator.

Figure 2:
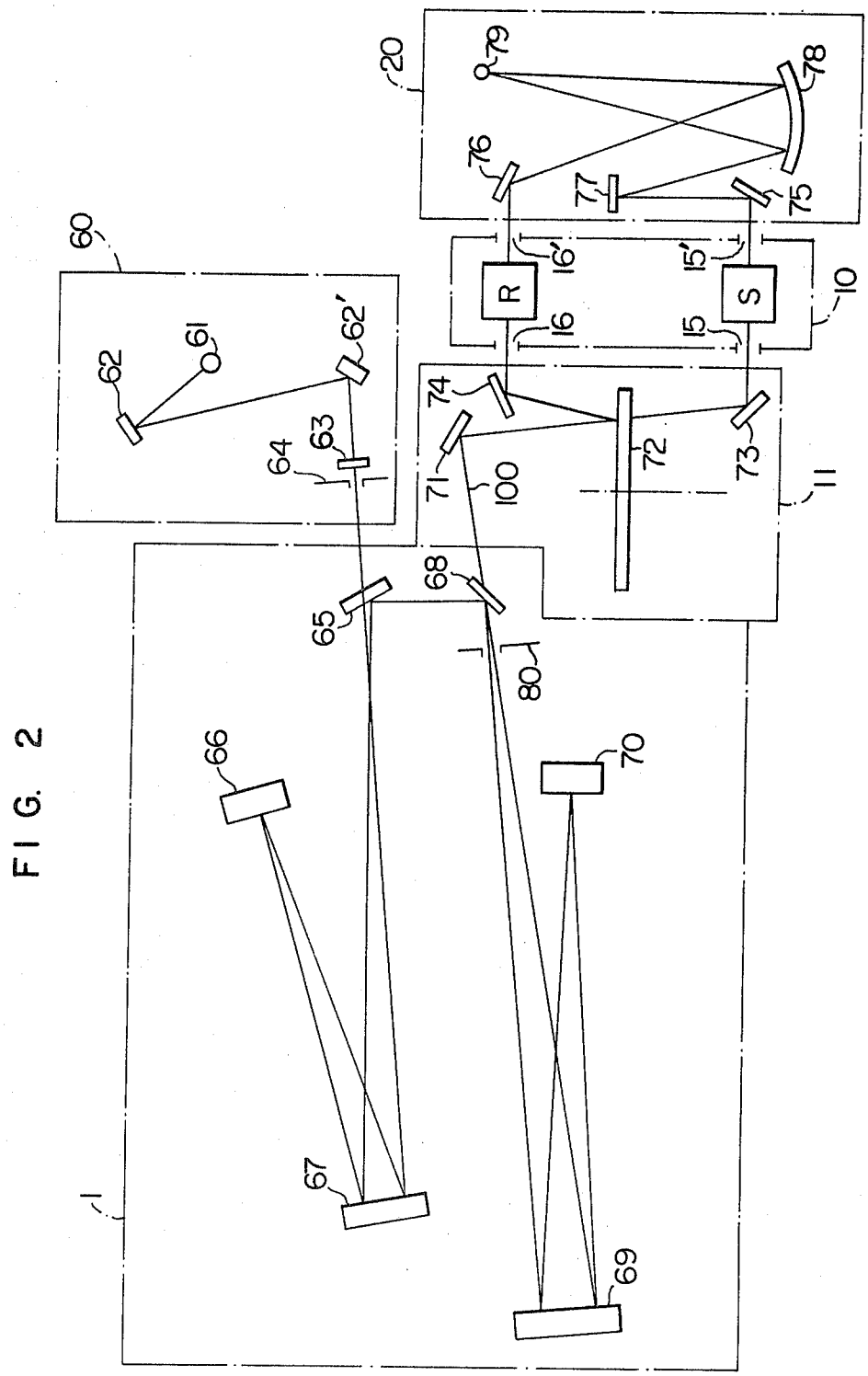
FIG. 2 shows a schematic diagram of an optical system generally incorporated with the spectrophotometer shown in FIG. 1.
Figure 7:
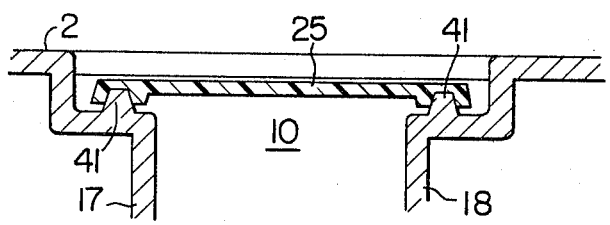

A typical structure of the optical system of the spectrophotometer will be explained in brief with reference to FIG. 2, for a better understanding of the invention. The light source device 60 includes a proper light source adapted to produce a desired wavelength of a measuring light such as tungsten filament lamp 61, a light source mirror 62, toroidal mirror 62', a filter 63 and a first slit 64. The light beam from the light source 61 is applied through the first slit 64 to the monochromator including plane mirrors 65, 68, first and second collimating mirrors 67, 69, first and second gratings 66 and 70, second and third slits 80, and toroidal mirror 71, thereby to form a measuring light beam 100 having a specific wavelength. The measuring light beam is divided to pass through two separate light paths by a sector mirror 72. The separate light beams are then reflected by plane mirrors 73 and 74, respectively, to be projected through the window 15 and 16 of the specimen chamber 10 onto a sample cell S and a reference cell R mounted therein. In the case of the measurement in the transmittance mode, the measuring light is applied, after passing through the respective cells, to a detector 20 through windows 15' and 16'. The detector 20 includes mirrors 75, 76, 77 and 78, and a photomultiplier 79. The output of the photomultiplier is processed in a known manner to obtain a signal representing spectrophotometric absorbance characteristics of the sample being measured, and it is recorded by the recorder 5 and also indicated by the indicator on the panel 6. Sections enclosed by a one-dot chain line in FIG. 2 correspond to the sections with the same reference numerals of the spectrophotometer explained referring to FIG. 1.

Referring to FIG. 1, the cover 2 has a side wall surrounding the side periphery of the housing and having an opening at the portion corresponding to the front side of the specimen chamber, and a top wall having an opening for the recorder 5 of the panel 6 and a rectangular opening serving as an opening through which one makes an access to the specimen chamber 10. A cover plate 25 with a knob 29 is provided to be slidable in a direction parallel to the top wall between an opening position where the specimen chamber is opened and a closing position where the chamber is closed. The case cover 2 has a partially elevated section 33 in which a power source circuit (not shown) is mounted.

Figure 3:
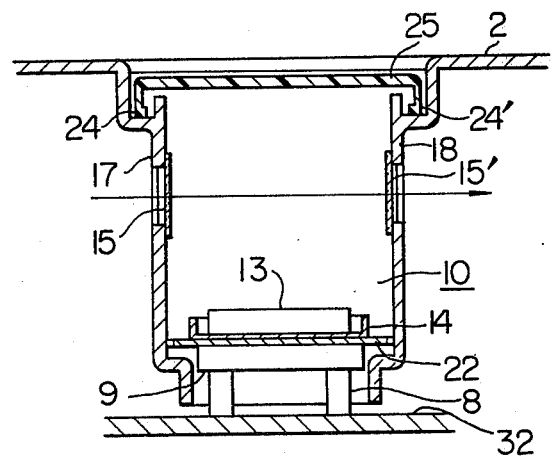
Figure 4:
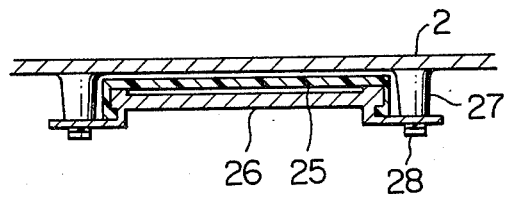

Referring now to FIGS. 3, 4 and 5 showing the cross sections taken along lines III—III, IV—IV, and V—V in FIG. 1, four sides of the specimen chamber 10 are defined by longitudinal side walls 17, 18, a rear wall 21 and a front wall 19. The longitudinal side walls 17, 18 and the rear wall 21 are formed integrally with the case cover 2, and their lower end portions extend closer to a base plate 32 attached to the bottom plate 7 on which the optical and electrical systems are mounted. A bottom wall 22 of the specimen chamber includes a front end portion which is folded and extends upwardly and to which the front wall 19 is integrally fixed. The bottom wall 22 is removably fixed by suitable fixtures (not shown) to a base block 9 which is fixed on four pillers 8 plated in the base 32. On the bottom wall 22, there are integrally formed a holder plate 13 on which a cell holder supporting the sample cell and the reference cell is mounted, and a receptacle 14 to receive any leakage of the samples positioned in the cells. When the bottom wall 22 is fixed to the block 9, the opposing side edges and the front edge of the bottom wall are closely in contact with the side walls 17 and 18 and the rear wall 21, respectively, and the front wall 19 closely contacts the front edges of the side walls 17 and 18.

In the side walls 17 and 18, windows 15 and 16, and 15' and 16' are formed to align with the optical paths of the measuring light beams reflected from the reflecting mirrors 73 and 74 of the monochromator and projected onto the reflecting mirrors 75 and 76 of the detector. In the windows, transparent window plates made of quartz, for example, are so fitted as to permit the measuring light beams to pass therethrough. When the cell holder for supporting the sample cell S containing a sample to be measured and the reference cell R containing a reference material is placed on the holder plate 13, the cells S and R are positioned on the optical paths.

A cover plate 25 made of opaque and, desirably, flexible material such as synthetic resin, aluminum sheet or the like is provided to close the opening defined by the top edges of the side walls 17 and 18, the front wall 19, and the rear wall 21, thereby to shield the specimen chamber from external light rays.

As well illustrated in FIG. 3, the joint portions of the side walls 17 and 18 and the cover 2 are shaped to provide grooves 24 and 24' having a U-shape cross section. The longitudinal opposing edge portions of the cover plate are bent to extend downwardly and the width of each of the bent portions is slightly longer than the depth of each of the grooves 24 and 24'. The end of each bent portion has an expanded portion extending along its entire length. The bent portions of the cover plate are loosely inserted into the grooves 24 and 24', respectively, in such a manner that the bottom faces of the expanded portions slidably contact with the bottom faces of the grooves 24 and 24', respectively. With this arrangement, light shielding is ensured between the cover plate 25 and the longitudinal opposite side edges of the opening of the specimen chamber, and further the cover plate is easily slidable between a closing position indicated by solid lines and an opening position indicated by dotted lines relative to the opening, as shown in FIG. 5. In the rear side of the specimen chamber and beneath the lower surface of the cover 2, there is provided a guide member 26 for supporting and guiding the cover plate 25 when it is moved from the closing position to the opening position, which is fixed to four bosses 27 on the cover 2 by means of screws 28. As shown in FIG. 4, the guide member 26 is formed with a cross section so as to provide slidable and complementary engagement with the bent portions having the expanded portions of the cover plate 25. A gap between the lower surface of the cover plate and the back wall 21 of the specimen chamber should be as small as possible but sufficient to permit a smooth sliding movement of the cover plate. The rear part of the cover plate is overlapped with the guide member when it is closed. In this way, the light seal between the cover plate and the rear edge of the specimen chamber opening is ensured.

The top edge of the front wall 19 of the specimen chamber is bent at a right angle and a permanent magnet member 30 is attached to the front wall 19 so as to extend in parallel to and along the substantially entire length of the bent portion thereby forming a groove 23 between the permanent magnet member 30 and the bent portion. The cover plate 25 is provided with an L-shaped metal fitting of magnetic material extending parallelly adjacent to the front edge of the cover plate. When the cover plate is in the closed position, the front end of the cover plate is inserted into the groove 23 and the L-shaped metal fitting intimately comes in contact with the magnetic member 30, thereby ensuring the light shield between the front edge of the opening of the specimen chamber and the cover plate, and further preventing the cover plate from inadvertently opening or vibrating, thereby preventing the generation of noise due to the vibration.

If the cover plate is made of flexible material, it is easily taken off from the specimen chamber when desired. In other words, as seen from FIGS. 3 and 5, the cover plate can be taken off easily by slightly lifting and pulling the front part under its half opening state. Also, the cover plate may easily be mounted to the specimen chamber merely by engaging the rear end of the cover plate with the guide member and inserting it thereinto by upwardly bending the front end. This is especially convenient when the measurement is conducted with a specific attachment mounted in the specimen chamber.

Figure 8:
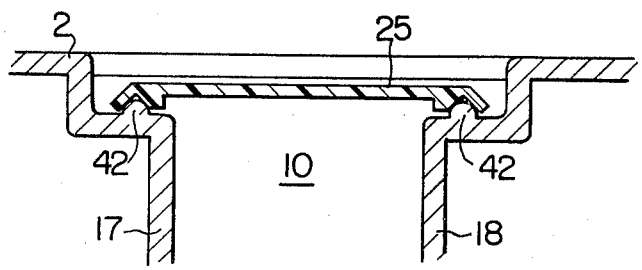
Figure 9:
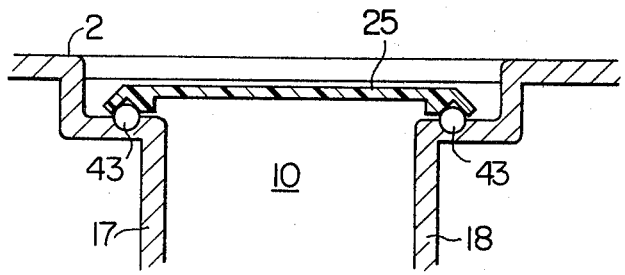

Other embodiments of the arrangement of the cover plate for light-shielding and slidable engagement with the walls defining the opening of the specimen chamber are shown in FIGS. 6 to 9. In the embodiment shown in FIG. 6, in order to facilitate smooth sliding of the cover plate, narrow and thin strips 34 and 34' made of a material having a small coefficient of friction such as fluorine-contained polymers sold as "Teflon" (trade name), for example, are respectively seated on the bottom surfaces of the grooves 24 and 24' of the side walls 17 and 18 so that the expanded portions of the bent portions of the cover plate slide over the strips 34 and 34', respectively. In the embodiment shown in FIG. 7, the upper portions of the side walls 17 and 18, are formed with shoulders, respectively, extending in parallel to the upper surface of the cover 2, and rails 41 having a trapezoidal cross section are provided to extent longitudinally on the shoulders, while the cover plate 25 is formed at both the longitudinal edge portions thereof with grooves complimentarily engageable with the rails 41. The embodiment shown in FIG. 8 is similar to that of FIG. 9, except that rails 42 having semicircle cross section are used in place of the trapezoidal rails 41 in FIG. 7 and the grooves of the cover plate are formed with inverse V-shape cross section so as to well engage with the semicircle rails. The embodiment shown in FIG. 9 is substantially the same as that of FIG. 8 except that the semicircle rails 42 of FIG. 8 are replaced by round rods 43 embedded in the shoulders with their upper halves projected over the shoulders. In those embodiments, the rails 41 and 42 may be formed integrally with the side walls by moulding the same material, and the rail 43 may be made of synthetic resin, aluminium or the like and fixed to the shoulders of the side walls by a suitable adhesive.

Figure 10:
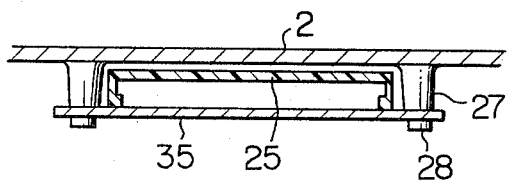
FIG. 10 shows a cross sectional view a modification of a member for guiding the sliding movement of the cover plate of the specimen chamber.

The guide member 26 which is provided at the rear of the specimen chamber may be simplified as a single plane board 35 as shown in FIG. 10. In this case, in order to get enough light-shield capability between the back wall of the specimen chamber and the cover plate, the gap between the cover 2 and the cover plate 25 is preferably kept as small as possible.

Since the specimen chamber of the invention has the construction as mentioned above, it has the following advantages.

1. The side walls and the rear wall of the specimen chamber are formed integral with the housing cover and therefore it is easy to assemble, and the light shield of the specimen chamber is improved because the joining parts where external light may leak are reduced.

2. As the cover plate slides backward and forward between the opening and closing positions, it is easy to open and close the opening of the specimen chamber and no additional space for the opening and closing operation is necessary.

3. The cover plate can be placed at any optional position between the opening and closing positions. For example, when an ordinary cell is placed on the path of the reference light through the transparent window 16, and a large attachment is placed on the path of the sample light through the transparent window 15, the cover plate may be placed in the middle between the opening and closing positions.

Therefore, the light-shielding can be easily achieved by covering a small cloth sheet over the half-opened opening of the specimen chamber or alternatively by providing the attachment with a suitable small cover plate adapted to shield the specimen chamber from external light in cooperation with the sliding cover plate.

4. As seen from FIG. 1, the power source section 33 is made higher than the main body 1 and the recording paper 3 runs over the rear side of the cover 2. Accordingly, the recording paper 3 moves over the back half of the upper surface of the cover 2. Accordingly, the recording paper almost never covers the opening of the specimen chamber 10, so that it is easy to change the sample cell or the cell holder containing the sample cell. Because of the sliding movement of the cover, the recording paper will never hinder the opening or closing of the sliding cover.

5. Since the cover plate may readily be mounted to and dismounted from the specimen chamber, it is convenient to place a special attachment to the specimen chamber.

6. The front wall 19 and the bottom wall 22 of the specimen chamber, the receptacle 14 and the holder 13 are removably mounted, as a unit, to the base 9. Accordingly, if necessary, by dismounting the assembly from the base, a special attachment can be mounted there for a special use.

7. It is easy to automate the opening and closing of the cover plate since it slides in rectilinear motion, as will be described later. Therefore, it is possible to incorporate a program for opening and closing the cover plate into a program for the computer control of the measuring process using the spectrophotometer.

Explanation will be made of an embodiment in which a motor drive opening/closing mechanism is used for the cover plate of the specimen chamber in the spectrometer according to the invention and the measuring process is interrelated with the opening and the closing of the cover plate.

Figure 11:
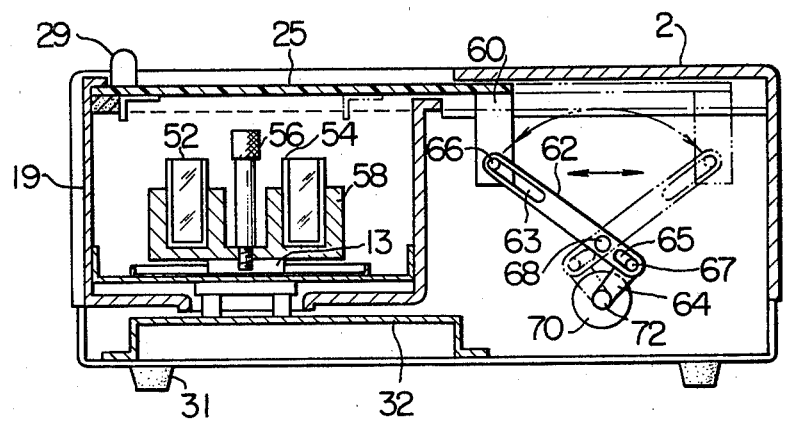
FIGS. 11 and 12 are cross sectional views of the specimen chamber having an automatic opening and closing mechanism of the cover plate.
Figure 12:
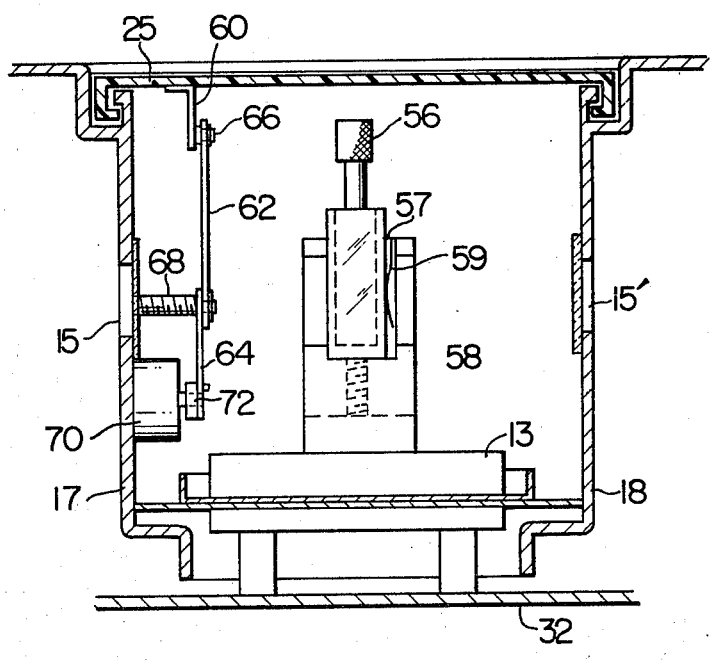

In FIGS. 11 and 12, a plate 60 with a pin 66 is fastened to the inside of the rear end part of the cover plate 25 in the specimen chamber. Crank arms 62 and 64 constitute a crank mechanism. The crank arm 62 pivotally mounted to a pivot 68 fixed to the rear extension of the side wall 17 of the specimen chamber, with one end having a narrow opening 63 into which the pin 66 is slidably inserted and the other end having a narrow opening 65 into which a pin 67 provided at one end of the crank arm 64 is slidably inserted. The other end of the crank arm 64 is fixed to a rotating shaft 72 of a drive motor, preferably a pulse motor. The rotating shaft 72 of the drive motor 70 is rotatable clockwise and counterclockwise between two angular positions under control of a drive control circuit to be described later and may be stopped at any optional position. At the terminating angular position of closkwise rotation of the rotating shaft 72, the cranks 62 and 64 are at the positions indicated by solid lines, and the cover plate 25 is at the closing position. When the rotating shaft 72 rotates counterclockwise, the crank arm 62 rotates clockwise around the shaft 68 by the crank mechanism to the position indicated by one-dot chain lines, and the cover plate 25 comes to the closed position.

Figure 13:
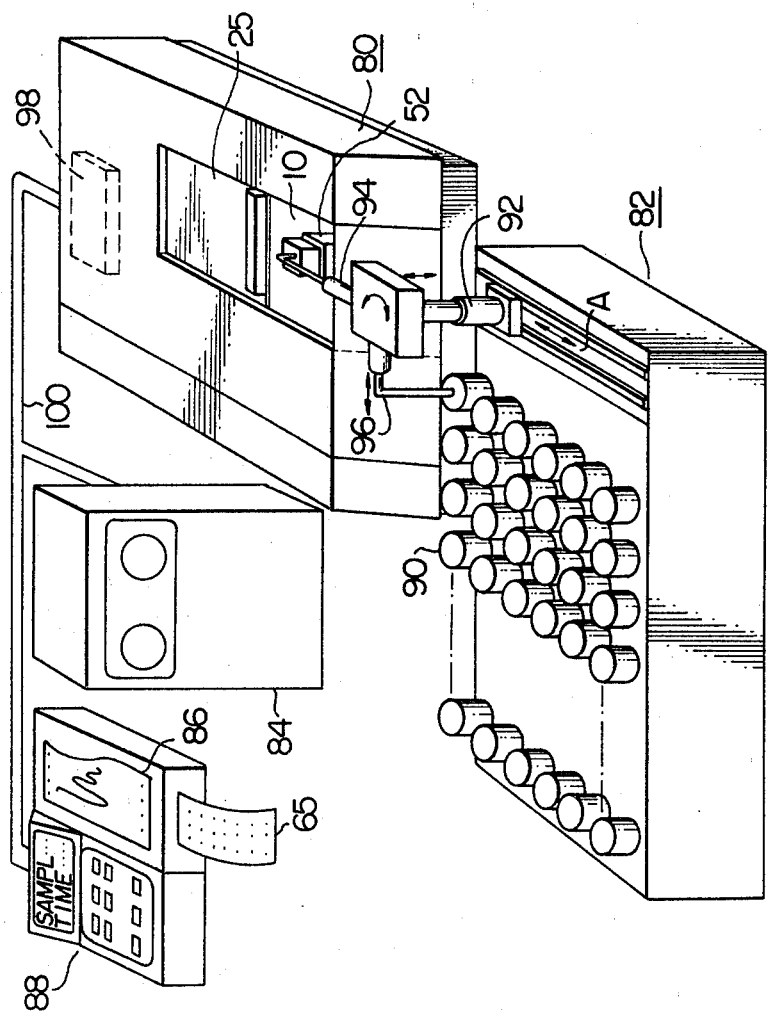
FIG. 13 shows a perspective view of a general arrangement of a computer control system of a spectrophotometer with a specimen chamber having an automatic opening and closing mechanism of its cover plate when used in combination with an automatic sampling device.

Explanation will be given of a case in which automatic measurement of a number of samples in succession by the spectrophotometer having the above-mentioned motor drive opening/closing mechanism of the cover plate for the specimen chamber associated with an automatic sampling mechanism of samples can be achieved. In FIG. 13 illustrating a general arrangement for performing such a measuring process, reference numeral 80 designates the spectrophotometer; 82 an automatic sampling device; 84 a computer for controlling the measuring process and operating the results of measurements; 86 an external recording device with an operating section 88; 100 an interface for operatively connecting the spectrophotometer 80, with the computer 84, and the external recording device. The spectrophotometer 80 includes a specimen chamber 10 and a drive control circuit 98 and the specimen chamber 10 is similar to that shown in FIG. 1. The drive control circuit 98 is comprised of a circuit for driving a drive motor 70 for opening and closing the cover plate 25 of the specimen chamber in response to given signals delivered from the computer 84, and a circuit for effecting an on/off control of an optical system of the spectrophotometer. The spectrophotometer 80 is shown to have neither recorder 5 nor panel 6 unlike that shown in FIG. 1 and instead there is provided, in this embodiment, an external recording device 86.

However, it will be understood that a spectrophotometer including a recorder similar to that shown in FIG. 1 may be used and either the internal recorder or the external one may be selectively used in the process. As shown in FIGS. 11 and 12, the cell holder 58 is removably mounted on the sample plate 13 of the specimen chamber by means of a screw 56. The cell holder 58 is provided with two cell receiving holes 74 in which a sample cell 52 for receiving a sample to be measured and a reference cell 54 for receiving a reference material are held, respectively. Generally, a square quartz cell is used for the sample cell but a tubular cell or a flow cell may be used in place of the square quartz cell. The holder 58 may be associated with a cooling water circulator (not shown) for limiting a temperature rise of the reference cell thereby keeping the temperature constant.

Returning to FIG. 13, in the automatic sampling device 82, many test tubes 90 containing reagent, wash water solution, diluted solution, oxidizing agent, or reducing agent and the like are disposed in rows and columns. A suction and feeding pipette 94 for sucking from and feeding into the sample cell 52 of the reagent and another pipette 96 for sucking and returning of the reagent from and to the test tube are supported by a carrier. Those pipettes are intercommunicated with each other. The carrier 92 is rotatable and is reciprocatably movable in a horizontal direction shown by an arrow and vertically up- and downwards. Further, it is provided with a driving device for effecting such movements.

The pipettes 94 and 96 are movable toward and away from the carrier by another driving device for effecting such movements in association with the pipettes. With the arrangement, by determining the position of the carrier 92 and the distances of the pipettes 94 and 96 from the carrier with respect to any desired test tube, the contents in the test tube may be transferred to the sample cell 52 and vice versa. Further, the automatic sampling device may be provided, if desired, with means for keeping the temperature of the test tube constant and vibrating means for vibrating the test tube at a given period and with a given amplitude.

For simplicity of explanation, let us consider a case where different samples to be measured are contained in the respective test tubes 90 and those samples are put into the sample cell 52 one after another for their measurement. The locations of those test tubes thus arranged and an order of the measurements of the samples are previously coded and stored in the computer. A measuring cycle of the sample of each test tube includes various steps such as transferring the reagent to the sample cell, executing the measurement, returning the reagent to the corresponding test tube after the measurement, and the like. The one measuring cycle is performed in the following steps in accordance with a program previously stored in the computer.

1. An operation start signal is applied to a computer by the operating section 88.
2. A position code of the test tube No. 1 containing a sample to be first measured is read out.
3. A position in a horizontal direction of a carrier and distances of extension of the pipettes 94 and 96 are determined in accordance with the position code read out.
4. Assuming that the carrier is at its upward position and the cover plate of the specimen chamber is at the opening position, commands are applied to the respective driving devices so that the carrier is horizontally moved to that determined position and the pipettes are extended to the correct distances.
5. A command to lower the carrier is issued, so that the carrier lowers and the pipette 94 is inserted into the sample cell 52 and the pipette 96 into the test tube.
6. A command to suck the sample by the pipette 96 is issued and the sucking device of the pipette 96 operates for a given time period to transfer a given amount of the sampe in the test tube No. 1 to the sample cell 52.

7. A command to lift the carrier is issued.

8. A command to move the cover plate 25 to the closing position is issued. Upon issuance of the command, the cover plate is moved to the closed position. When the cover plate reaches the closed position, a proper sensor (not shown) produces a closed position signal.

9. The measurement by the spectrophotometer starts upon issuance of the closing position signal.

10. The results of the measurement are stored in the computer 63 and applied to the recording device 86 to be recorded and displayed, if necessary.

11. A command is issued to move the cover plate of the specimen chamber from the closed position to the open position.

12. After the cover plate reaches the open position, a command to lower the carrier is produced.

13. After the carrier 92 lowers and the pipettes 94 and 96 are inserted into the sample cell 52 and the test tube No. 1, a command to suck the sample by the pipette 94 is produced so that sample in the sample cell is returned to the test tube No. 1.

14. A command to lift the carrier is produced. Upon executing this step, the measuring cycle of the sample in the sample tube No. 1 is completed.

15. Then, the position of the test tube No. 2 containing a sample to be next measured is read out and the next measuring cycle initiating at the step 2 is repeated for the test tube No. 2.

The above-mentioned embodiment is an example in which the spectrophotometer according to the invention is combined with the automatic sampling device and the opening and closing of the cover plate of the specimen chamber are automatically controlled in accordance with the operation of the sampling device. It is apparent to those skilled in the art that the spectrophotometer of the invention may be combined with any proper external device other than the automatic sampling device for automatic measuring of samples, and the signals used for the automatic measurement are used for the automatic control of the opening and the closing of the cover plate of the specimen chamber.

We claim:

1. A spectrophotometer including a housing; an optical system mounted in said housing for generating a measuring light beam; and a specimen chamber provided in said housing for mounting therein a sample cell to be analyzed by applying thereto said measuring light beam, said specimen chamber being formed with an opening through which said chamber is accessible from outside of said housing for mounting or dismounting the sample cell, a generally-rectangular cover plate made of an opaque material and adapted to cover said opening of said specimen chamber, and means for mounting said cover plate so as to be slidably movable between a closing position where said cover plate wholly covers said opening thereby shielding said specimen chamber from external light and an opening position where said specimen chamber is accessible from outside of said housing, said chamber having opposing side walls, a rear wall connected to the rear ends of said side walls, and a front wall extending between the front ends of said side walls, said cover plate having a bent portion formed by bending opposing side edges of said cover plate inwardly, and said mounting means including portions extending along the entire length of the upper edges of said side walls and slidably supporting said bent portions of said cover plate, respectively; said housing including a bottom plate, and a cover for defining a space for accommodating said optical system in cooperation with said bottom plate and including an upper wall and a side wall extending between said upper wall and said bottom plate, said specimen chamber being provided by partitioning said space, the opening of said specimen chamber being formed by cutting off a substantially-rectangular portion of the upper wall of said cover, and said opposing side walls and said rear wall of said specimen chamber being formed integrally with said cover to extend from the peripheral edge of said cut-off portion of said upper wall into said space.

2. A spectrophotometer including a housing; an optical system mounted in said housing for generating a measuring light beam; and a specimen chamber provided in said housing for mounting therein a sample cell to be analyzed by applying thereto said measuring light beam, said specimen chamber being formed with an opening through which said chamber is accessible from outside of said housing for mounting or dismounting the sample cell, a generally-rectangular cover plate made of an opaque material and adapted to cover said opening of said specimen chamber, and means for mounting said cover plate so as to be slidably movable between a closing position where said cover plate wholly covers said opening thereby shielding said specimen chamber from external light and an opening position where said specimen chamber is accessible from outside of said housing, said chamber having opposing side walls, a rear wall connected to the rear ends of said side walls, and a front wall extending between the front ends of the side walls, said cover plate having a bent portion formed by bending opposing side edges of said cover plate inwardly, and said mounting means including portions extending along the entire length of the upper edges of said side walls and slidably supporting said bent portions of said bent portions of said cover plate, respectively; said portions for supporting said bent portions of said cover plate each being in the form of a groove so as to receive said bent portion, and said bent portions of said cover plate each having at the end thereof an expanded portion with a longitudinally-extending plane surface closely in contact with the bottom surface of said groove; said housing including a bottom plate, and a cover for defining a space for accommodating said optical system in cooperation with said bottom plate and including an upper wall and a side wall extending between said upper wall and said bottom plate, said specimen chamber being provided by partitioning said space, the opening of said specimen chamber being formed by cutting off a substantially-rectangular portion of the upper wall of said cover, and said opposing side walls and said rear wall of said specimen chamber being formed integrally with said cover to extend from the peripheral edge of said cut-off portion of said upper wall into said space.

3. A spectrophotometer according to claim 1 or 2, in which the opening formed by cutting away the upper wall of said cover extends to an opening formed by cutting off a part of the side wall of said cover, the front wall of said specimen chamber being formed to cover the opening formed in the side wall of said cover and being substantially flush with the side wall of said cover, and said specimen chamber further including a substantially rectangular bottom wall having a front edge integrally connected with said front wall and opposing side edges and a rear edge closely in contact with said opposing side walls and said rear wall of said specimen chamber.

4. A spectrophotometer according to claim 3, in which a base plate for mounting the optical system is fixed to the bottom plate of said housing, the bottom wall of said specimen chamber being removably fixed to said base plate, and a base block on which the sample cell is mounted being fixed to the upper surface of said bottom wall.

5. A spectrophotometer according to claim 1 or 2, in which said cover plate for covering the opening of said specimen chamber is movable parallel to the inner side of the upper wall of said housing cover and means is provided at the inner side of said housing cover for guiding said cover plate when it moves to the opening position.

6. A spectrophotometer according to claim 5, in which said guiding means includes a guide member which is fixed to the inner side of the upper wall of said housing cover to extend parallel thereto and has portions for supporting the bent portions of said cover plate when it moves from the closing position to the opening position.

7. A spectrophotometer according to claim 6, in which said cover plate is formed to have a length in its sliding direction longer than that of the opening of said specimen chamber in the same direction and a rear edge extending up to the middle of said guide member when it is at its closing position, and said cover plate is made of a flexible material for facilitating mounting and dismounting thereof to and from said specimen chamber by bending said cover plate.

8. A spectrophotometer according to claims 1 or 2, in which a thin strip made of material having a small coefficient of friction is seated on the bottom of said groove to extend along the entire length of the groove, and the elongated plane surface of said expanded portion closely comes in contact with said sheet.

9. A spectrophotometer according to claims 1 or 2, in which said cover plate is provided with projections extending parallel to and separated from the bent portions of said cover plate so as to provide grooves between said projections and said bent portions, respectively, and said portions for supporting said bent portions of said cover plate include elongated projections so formed as to slidably engage with said grooves.

10. A spectrophotometer according to claim 9, in which said grooves are formed to have an inverse V-shape cross section and said elongated projections are formed to have a semicircular cross section engageable with said groove.

* * * * *